United States Patent [19]

Chang et al.

[11] Patent Number: 4,546,093
[45] Date of Patent: Oct. 8, 1985

[54] PREPARATION OF CATALYST SYSTEM FOR THE SYNTHESIS OF 2-6-XYLENOL

[75] Inventors: Kong R. Chang; Trong G. Lin, both of Taichung, Taiwan

[73] Assignee: China Petrochemical Development Corp., Taipei, Taiwan

[21] Appl. No.: 628,103

[22] Filed: Jul. 5, 1984

[51] Int. Cl.$^4$ .................. B01J 23/34; B01J 27/24; B01J 27/02
[52] U.S. Cl. ........................ 502/324; 502/201; 502/217
[58] Field of Search ............ 502/201, 324, 217; 568/804

[56] References Cited

U.S. PATENT DOCUMENTS

| Re. 30,083 | 8/1979 | Reilly et al. ............ 502/324 X |
| 3,214,236 | 10/1965 | Weisz et al. ............ 502/324 X |
| 3,716,479 | 2/1973 | Weisz et al. ............ 502/324 X |
| 3,852,370 | 12/1974 | Henkson et al. ............ 502/324 X |
| 3,922,872 | 12/1975 | Reilly et al. ............ 502/324 X |
| 3,951,869 | 4/1976 | Baker ............ 502/324 |
| 3,998,760 | 12/1976 | Christmann et al. ............ 502/324 |
| 4,149,997 | 4/1979 | Araki et al. ............ 502/324 X |
| 4,233,186 | 11/1980 | Duprez et al. ............ 502/324 X |

FOREIGN PATENT DOCUMENTS

| 2237458 | 2/1973 | Fed. Rep. of Germany ...... 502/324 |
| 2801783 | 8/1978 | Fed. Rep. of Germany ...... 502/324 |
| 49-5928 | 1/1974 | Japan . |

OTHER PUBLICATIONS

80 Chem. Abstr. No. 120522v (1974).

*Primary Examiner*—D. E. Gantz
*Assistant Examiner*—William G. Wright
*Attorney, Agent, or Firm*—Cushman, Darby & Cushman

[57] ABSTRACT

A process for preparing a 3-component catalyst system consisting of manganic oxide, ferric oxide and zinc oxide, which are adjusted to have an atomic ratio of Mn:Fe:Zn from 90:20:20 to 99:0.01:0.01, is used for the catalytic synthesis of 2,6-xylenol from reacting phenol with methanol.

7 Claims, No Drawings

PREPARATION OF CATALYST SYSTEM FOR THE SYNTHESIS OF 2-6-XYLENOL

BACKGROUND OF THE INVENTION 2,6-xylenol is produced by catalytically reacting phenol and methanol in a fixed-bed reactor under reaction conditions of normal pressure, gaseous phases and high temperature ranging from 300° C. to 650° C. The 2,6-xylenol is polymerized as poly-phenylene oxide which is a valuable engineering plastic material suitable for engineering and commercial applications by its good properties, such as: corrosion resistance and resistance to cold or hot water.

A conventional catalyst was disclosed by Arakawa Forest Chemical Industries, Ltd. in Japan Invention Publication No. 49-5928 (copy enclosed herewith as reference) for catalytic synthesis of 2,6-xylenol by mixing manganic oxide with ferric oxide, or by mixing manganic oxide with zinc oxide. However, such a conventional catalyst has the following defects:

1. The reaction of phenol and methanol to produce 2,6-xylenol is subjected to gaseous phases and exothermic reaction. If increasing the reaction temperature and pressure, the selectivity of product will be reduced and by-products will be increased to reduce the productivity. The major by-product is 2,4,6-trimethyl phenol which is very difficult to separate from the desired 2,6-xylenol.

Due to this reason, Arakawa process for synthesizing 2,6-xylenol was performed under normal pressure (1 Kg/cm$^2$). In Arakawa process, if the Mn-Fe catalyst and the following reaction conditions are used:

Atomic ratio: Mn:Fe=99:1,
Reaction temperature: 400° C.,
Charging rate: 15 ml/hr,
Liquid weight hourly space velocity (WHSV); b 0.439 l/hr, the productivity of 2,6-xylenol is very low and is only 0.1669 g/g-cat.hr.

2. During the synthesis of 2,6-xylenol by reacting phenol and methanol, methanol is consumed and decomposed into carbon monoxide and hydrogen. The consumption of methanol will reduce the concentration of methanol for the reaction and thus reduce the conversion rate of phenol and reduce the selectivity to 2,6-xylenol. If the yield of 2,6-xylenol is 94.70%, the methanol utilization efficiency is only 36.35%. Such a low methanol utilization efficiency is too low to have economic commercial value.

3. When making the catalyst by Arakawa process, the nitrate salts are decomposed into oxides which will release poisonous nitrogen dioxide to cause hazardous air pollution. The nitrogen dioxide will also react with water to form nitric acid which will corrode the contacted equipments.

4. The catalyst oxides of Arakawa process are formed through hot-melting decomposition so that the formed oxides have great density and are difficult for final processing.

The present inventors have found the defects of Arakawa process as abovementioned and invented the present process for making catalyst system for the synthesis of 2,6-xylenol.

SUMMARY OF THE INVENTION

The object of the present invention is to provide a 3-component catalyst system consisting of manganic oxide, ferric oxide and zinc oxide for catalytically reacting phenol with methanol to produce 2,6-xylenol with higher productivity. The catalyst is produced with no air pollution or corrosion problem in comparison with conventional catalysts.

DETAILED DESCRIPTION

In accordance with the present invention, a reactor filled with water is charged with manganic nitrate, ferric nitrate and zinc nitrate. The raw materials in the reactor is agitated for complete mixing and an aqueous alkaline solution is added into the reactor for co-precipitation of hydroxides. The precipitates are then filtered and washed by water to remove impurities and ions. The washed precipitates are dried overnight in an oven at 160° C. to form a mixture of oxides. The formed oxides are put into an extruder to form a bar-like product which is then cut to form granules with the desired size. The granules are placed in a calcinator for calcination of three hours under air flow and temperature range from 300° C. to 650° C. to activate the catalyst of the present invention.

Besides the aforementioned nitrates, other metallic salts such as: chlorates, sulfates, acetates, oxalates or other halogen salts or acid salts can also be used to form metallic oxides for the present invention. The alkaline solutions are ammonia water, aqueous caustic soda and potassium hydroxide.

The detailed process for preparing catalyst system of the present invention and the efficiency of the present catalyst used for synthesizing 2,6-xylenol is described hereinafter in the following examples:

EXAMPLE 1

In a reactor provided with an agitator, 500 grams $Mn(NO_3)_2.6H_2O$, 3.5 g $Fe(NO_3)_3.9H_2O$, 2.3 g $Zn(NO_3)_2.4H_2O$ and 600 ml water are added and homogeneously mixed. Ammonia water (25%) is added into the reactor until PH value of the solution is 9. The addition of ammonia water is then stopped and the co-precipitation of manganic hydroxide, ferric hydroxide and zinc hydroxide is formed. The precipitates are washed several times with water and then dried overnight at 160° C. in an oven. By the way, the hydroxides are decomposed to oxides which are extruded to form granules each having a dimension of 4 mm$\phi \times$5 mm L. The granules are calcinated at 650° C. under incoming air flow for three hours to activate the catalyst. The atomic ratio of Mn:Fe:Zn of this catalyst is 99:0.5:0.5.

Phenol, methanol and water are mixed in a container equiped with a measuring pump to obtain mixed reactants in which the mole ratio of phenol:methanol:water is 1:6:1. The reactants are charged into a fixed-bed reactor previously filled with 50 g catalyst made as aforementioned. The reaction is performed under normal pressure and 450° C. The products are cooled through a condenser and then separated in a gas-liquid separator, from which the liquid product is collected from the lower end of the separator and the gaseous product is collected from the upper end thereof. The collected products are analysed by gas chromatography to identify the major product as 2,6-xylenol. The related operation data are shown in Table 1.

EXAMPLE 2

By using the method as described in Example 1, the mole ratio of the reacting metallic salts is modified to produce catalyst systems with different atomic ratio of Mn, Fe and Zn and other operation data for synthesizing 2,6-xylenol, such as: reaction temperature, flow rate and liquid weight hourly space velocity (WHSV) of the reactants are adjusted to obtain the results as shown in Table 1.

EXAMPLE 3

By using the process as mentioned in Example 1, the operation data are modified as follows:

Reaction temperature: 520° C.
Total reaction pressure: 10 Kg/cm$^2$
Reactants flow rate: 129.75 ml/hr
WHSV: 2.273 l/hr the productivity of 2,6-xylenol is 0.86 g/g.cat.hr which is 5.15 times of the yield 0.1669 g/g.cat.hr of Arakawa process by using 2-component catalyst (Mn:Fe=99:1). Hence, the yield of the present invention is greatly increased even by raising reaction temperature and pressure than that of the conventional process.

TABLE 1

| Catalyst Composition Atomic Ratio = Mn:Fe:Zn | Reaction Temperature °C. | Reactants Flow Rate ml/hr | WHSV l/hr | Conversion Rate of Phenol$^a$ % | Selectivity to 2,6-Xylenol$^b$ % |
| --- | --- | --- | --- | --- | --- |
| 99:1:1 | 450 | 24.35 | 0.43 | 99.95 | 96.01 |
| 99:1:1 | 487 | 48.29 | 0.85 | 99.49 | 91.37 |
| 90:10:10 | 455 | 24.35 | 0.43 | 99.82 | 94.24 |
| 99:0.5:0.5 | 460 | 39.56 | 0.70 | 99.83 | 94.67 |
| 99:0.5:0.5 | 470 | 49.82 | 0.88 | 99.00 | 90.98 |
| 99:1:0.5 | 455 | 28.95 | 0.51 | 99.27 | 91.50 |
| 99:1:0.5 | 490 | 48.30 | 0.85 | 98.72 | 91.08 |
| 99:0.1:0.1 | 450 | 28.13 | 0.50 | 99.97 | 92.35 |
| 99:0.1:0.1 | 490 | 51.18 | 0.90 | 99.97 | 90.54 |
| 99:0.5:0.5$^c$ | 450 | 26.55 | 0.465 | 99.88 | 95.28 |

Notes $^a$Conversion rate of phenol (%) = $\dfrac{\text{Moles of phenol participating in the reaction}}{\text{Moles of Phenol existing in reactants}} \times 100$ $^b$Selectivity to 2,6-xylenol (%) = $\dfrac{\text{Moles of 2,6-xylenol}}{\text{Moles of phenol participating in the reaction}} \times 100$ $^c$In Example 1, methanol utilization efficiency (%) = $\dfrac{\text{Ortho-cresol produced (mole/hr)} + \text{2,6-xylenol produced (mole/hr)} \times 2}{\text{Methanol consumed in reaction (mole/hr)}} \times 100$ The methanol utilization efficiency of Example 1 is 52.63% which is greater than the efficiency of Arakawa process.

The catalyst of the present invention is produced by co-precipitation method wherein the oxides are formed from hydroxides with the release of non-toxic moisture which will not cause air pollution and corrosion to the equipments. As the catalyst of the present invention is produced by precipitation and drying method so that the product has better processing properties and is easy for grinding and extruding. Hence, the present invention is superior to Arakawa process.

We claim:

1. A process for the preparation of a catalyst system used for synthesizing 2,6-xylenol, which comprises:
   A. mixing manganic, ferric, and zinc salts to have atomic ratios of Mn:Fe:Zn from 90:20:20 to 99:0.01:0.01 in a water solution;
   B. adding an aqueous alkaline solution to said solution of step A until the PH value is 9 for co-precipitation of hydroxides of Mn, Fe and Zn;
   C. treating the precipitates by filtration, water washing and drying the washed precipitates at 160° C. to form oxides of Mn, Fe and Zn; and
   D. extrusion and granulation of said oxide mixture by calcination at 300°-650° C. under incoming air flow for 3 hours to activate the catalyst system.

2. A process according to claim 1, wherein the atomic ratio of Mn:Fe:Zn is preferably ranging from 90:10:10 to 99:0.05:0.05.

3. A process according to claim 1, wherein said salts of Mn, Fe and Zn are halogen salts.

4. A process according to claim 1, wherein said salts of Mn, Fe and Zn are acid salts of sulfates, acetates or oxalates.

5. A process according to claim 1, wherein said aqueous alkaline solution is ammoniacal, aqueous caustic soda solution or potassium hydroxide solution.

6. A catalyst obtained in accordance with claim 1, wherein said catalyst consists of a three component system composed of manganic oxide, ferric oxide, and zinc oxide wherein the atomic ratio of said oxides ranges from 90:20:20 to 99:0.01:0.01/

7. A process according to claim 1 wherein said salts of Mn, Fe and Zn are nitrate salts.

* * * * *